United States Patent [19]
Lechot

[11] Patent Number: 6,129,732
[45] Date of Patent: Oct. 10, 2000

[54] SURGICAL REAMER

[75] Inventor: André Lechot, Orvin, Switzerland

[73] Assignee: Precifar S.A., Orvin, Switzerland

[21] Appl. No.: 09/414,171

[22] Filed: Oct. 7, 1999

[30] Foreign Application Priority Data

Oct. 9, 1998 [CH] Switzerland ............... 2042/98

[51] Int. Cl.⁷ .................................................. A61B 17/16
[52] U.S. Cl. ................................................ 606/80; 606/81
[58] Field of Search .................................. 606/79, 80, 81, 606/85, 86, 87, 89; 76/13, 101.1, 115; 623/22, 23

[56] References Cited

U.S. PATENT DOCUMENTS

| | | | |
|---|---|---|---|
| 5,462,548 | 10/1995 | Pappas et al. | 606/80 |
| 5,658,290 | 8/1997 | Lechot | 606/80 |
| 5,904,688 | 5/1999 | Gilbert et al. | 606/86 |
| 5,980,170 | 11/1999 | Salyer | 606/80 |
| 6,001,105 | 12/1999 | Sayler | 606/81 |
| 6,027,503 | 2/2000 | Khalili et al. | 606/81 |

Primary Examiner—John J. Wilson
Assistant Examiner—Philogene Pedro
Attorney, Agent, or Firm—Bugnion S.A.; John Moetteli

[57] ABSTRACT

A surgical reamer in the form of a cap (1) fitted with arms (4) extending from the circular edge of the reamer toward the axis of the reamer for its attachment to a reamer spindle. The reamer comprises a central disk (3) to which said arms (4) are attached. The disk is intended to display an item of information, in particular the diameter of the reamer. In this way, the diameter of the reamer or any other information may be read without handling the reamer and turning it upward.

2 Claims, 1 Drawing Sheet

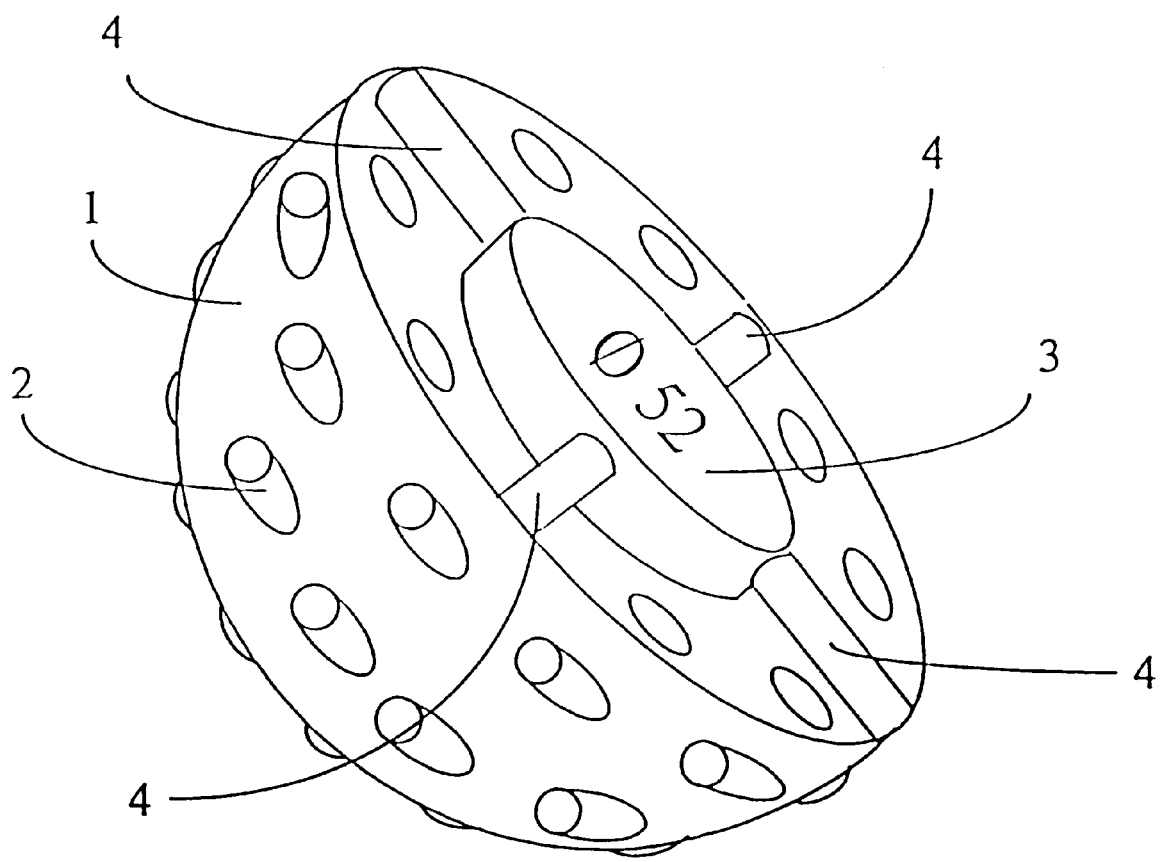

SURGICAL REAMER

BACKGROUND OF THE INVENTION

The present invention relates to a surgical reamer in the form of a cap of circular section equipped with arms extending radially from the circular edge of the reamer toward the axis of the reamer for its attachment to a reamer spindle.

A reamer of this type is known from Patent Application EP 0,704,191, the content of which is incorporated by reference, in the name of the applicant. In this document, the cap is hemispherical and equipped with four arms arranged in a cross for the bayonet-type attachment of the reamer to a reamer spindle. The cap may be of non-spherical shape, especially conical shape. These reamers are produced with various diameters, the diameter being selected as needed. For their sterilization, the reamers are suspended with the apex of the cap facing downward. However, the diameter of the reamer is indicated on the outer surface of the cap, which makes it necessary to handle the reamer and turn it upward in order to read its diameter and so find the reamer required.

The object of the present invention is to allow easy reading of the diameter of the reamer or any other information without it being necessary to handle the reamer and turn it upward.

The surgical reamer according to the invention is a reamer comprising a central disk arranged parallel to the attachment arms and to which said arms are attached, said disk being intended to display an item of information, in particular the diameter of the reamer.

The disk is preferably circular but it could equally well be of any other shape.

The radial arms can conveniently be solidly attached to the disk, in particular by being embedded therein, so that the disk in no way weakens the attachment of the reamer to its reamer spindle. The protruding length of the radial arms is in all cases entirely sufficient for the attachment of the reamer to the reamer spindle, whether this is a reamer spindle as described in Patent Application EP 0,704,191 or another reamer spindle, for example a reamer spindle as described in Patent FR 2,281,095, the content of which is incorporated by reference.

The strength of the attachment of the reamer to its reamer spindle is not affected by the disk, and indeed the latter may increase this strength.

BRIEF DESCRIPTION OF THE DRAWINGS

The attached drawing shows, by way of example, an embodiment of the invention.

DETAILED DESCRIPTION OF THE PREFERRED EMBODIMENT(S)

The single FIGURE of the drawing is a perspective view of a surgical reamer of the type described in Patent Application EP 0,704,191, that is to say, a reamer for the shaping of the cotyloid cavity in the event of a replacement of the hip joint by total prosthesis. This reamer comprises a hemispherical cap 1 equipped with cutting edges 2 made by cutting out and folding back the material. The center of the base of the cap 1 is occupied by a circular steel disk 3 in which four arms 4, arranged in a cross, are radially attached by embedding, the other ends being welded to the cap 1. The diameter of the reamer is inscribed on the disk 3 and in the example shown is 52 millimeters.

The arms 4 could, of course, be made integrally with the disk 3, and the disk could be of any other shape.

Although illustrative embodiments of the invention have been shown and described, a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed:

1. A surgical reamer in the form of a cap (1) of circular section and having a circular edge and an axis, the cap equipped with arms (4) extending from the circular edge toward the axis of the reamer for attachment of the reamer to a reamer spindle, wherein the reamer comprises a central disk (3) arranged parallel to the plane of said arms (4) and to which said arms are attached, said disk displaying an item of information, in particular the diameter of the reamer.

2. The reamer as claimed in claim 1, wherein the radial arms (4) are embedded in the disk (3).

* * * * *